US011439325B2

(12) United States Patent
Zanotto et al.

(10) Patent No.: US 11,439,325 B2
(45) Date of Patent: Sep. 13, 2022

(54) WIRELESS AND RETROFITTABLE IN-SHOE SYSTEM FOR REAL-TIME ESTIMATION OF KINEMATIC AND KINETIC GAIT PARAMETERS

(71) Applicants: THE TRUSTEES OF THE STEVENS INSTITUTE OF TECHNOLOGY, Hoboken, NJ (US); THE TRUSTEES OF COLUMBIA UNIVERSITY IN THE CITY OF NEW YORK, New York, NY (US)

(72) Inventors: Damiano Zanotto, Jersey City, NJ (US); Sunil K. Agrawal, Newark, DE (US); Huanghe Zhang, Jersey City, NJ (US)

(73) Assignees: THE TRUSTEES OF THE STEVENS INSTITUTE OF TECHNOLOGY, Hoboken, NJ (US); THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 452 days.

(21) Appl. No.: 16/457,730

(22) Filed: Jun. 28, 2019

(65) Prior Publication Data

US 2020/0000375 A1 Jan. 2, 2020

Related U.S. Application Data

(60) Provisional application No. 62/692,568, filed on Jun. 29, 2018.

(51) Int. Cl.
*A61B 5/11* (2006.01)
*A61B 5/103* (2006.01)
*A61B 5/00* (2006.01)

(52) U.S. Cl.
CPC ............ *A61B 5/112* (2013.01); *A61B 5/0004* (2013.01); *A61B 5/1038* (2013.01);
(Continued)

(58) Field of Classification Search
CPC ..... A61B 5/112; A61B 5/0004; A61B 5/1038; A61B 5/1112; A61B 5/486; A61B 5/6807;
(Continued)

(56) References Cited

U.S. PATENT DOCUMENTS 6,145,389 A 11/2000 Ebeling et al.
7,717,826 B2 5/2010 Cox et al.
(Continued)

FOREIGN PATENT DOCUMENTS

DE 102015007106 A1 * 12/2016 ............. G01G 19/52
WO WO-2017058913 A1 * 4/2017 ........... A61B 5/1117

OTHER PUBLICATIONS

Zhang, et al., "Estimating CoP Trajectories and Kinematic Gait Parameters in Walking and Running Using Instrumented Insoles," IEEE Robotics and Automation Letters, vol. 2, No. 4, Oct. 2017, pp. 2159-2165.

(Continued)

*Primary Examiner* — Patrick Fernandes
(74) *Attorney, Agent, or Firm* — Lewis Roca Rothgerber Christie LLP

(57) ABSTRACT

A quantitative gait training and/or analysis system includes one or more footwear modules that may include a piezoresistive sensor, an inertial sensor and an independent logic unit. The footwear module functions to permit the extraction of gait kinematics and evaluation thereof in real time, or data may be stored for later reduction and analysis. Embodiments relating to calibration-based estimation of kinematic gait parameters are described.

33 Claims, 3 Drawing Sheets

(52) U.S. Cl.
CPC ............ *A61B 5/1112* (2013.01); *A61B 5/486* (2013.01); *A61B 5/6807* (2013.01); *A61B 5/7264* (2013.01); *A61B 2505/09* (2013.01); *A61B 2562/0247* (2013.01); *A61B 2562/046* (2013.01)

(58) Field of Classification Search
CPC ............ A61B 5/7264; A61B 2505/09; A61B 2562/0247; A61B 2562/046; A61B 5/22; A43B 3/0031; A43B 3/0005; A63B 71/0622; G06K 9/00342
See application file for complete search history.

(56) References Cited

U.S. PATENT DOCUMENTS

| | | | |
|---|---|---|---|
| 8,109,890 | B2 | 2/2012 | Kamiar et al. |
| 9,179,862 | B2 | 11/2015 | Stergiou et al. |
| 9,198,821 | B2 | 12/2015 | Unluhisarcikli et al. |
| 9,307,932 | B2 | 4/2016 | Mariani et al. |
| 9,470,705 | B2 | 10/2016 | Statham |
| 9,681,826 | B2 | 6/2017 | Dunias et al. |
| 9,687,712 | B2 | 6/2017 | Statham et al. |
| 9,713,439 | B1 | 7/2017 | Wu et al. |
| 2006/0282017 | A1* | 12/2006 | Avni ................... A61B 5/22 600/587 |
| 2007/0203435 | A1 | 8/2007 | Novak |
| 2009/0240171 | A1* | 9/2009 | Morris Bamberg . A61B 5/1038 600/595 |
| 2010/0004566 | A1* | 1/2010 | Son ..................... A43B 3/0005 600/592 |
| 2011/0054358 | A1* | 3/2011 | Kim .................... A61B 5/1038 600/592 |
| 2011/0054359 | A1* | 3/2011 | Sazonov .............. A61B 5/4866 600/595 |
| 2012/0116550 | A1* | 5/2012 | Hoffman ............ A63B 71/0622 700/91 |
| 2013/0041617 | A1* | 2/2013 | Pease ................... A43B 3/0031 702/139 |
| 2013/0096466 | A1* | 4/2013 | Sarrafzadeh ......... A61B 5/1038 600/592 |
| 2015/0182843 | A1* | 7/2015 | Esposito ............ G06K 9/00342 700/91 |
| 2016/0331557 | A1 | 11/2016 | Tong et al. |
| 2017/0055880 | A1 | 3/2017 | Agrawal et al. |

OTHER PUBLICATIONS

Zhang, et al., "Regression Models for Estimating Kinematic Gait Parameters with Instrumented Footwear," In Proc of the 7th IEEE International Conference on Biomedical Robotics and Biomechatronics (Biorob), Enschede, The Netherlands, Aug. 26-29, 2018, pp. 1169-1174.

Crea, et al., "A Wireless Flexible Sensorized Insole for Gait Analysis," Sensors, vol. 14, Jan. 9, 2014, pp. 1073-1093.

Lugade, et al., "Center of mass and base of support interaction during gait," Gait & Posture 33, 2011, pp. 406-411.

\* cited by examiner

WIRELESS AND RETROFITTABLE IN-SHOE SYSTEM FOR REAL-TIME ESTIMATION OF KINEMATIC AND KINETIC GAIT PARAMETERS

CROSS-REFERENCE TO RELATED APPLICATION

This application claims priority to U.S. Provisional Patent Application Ser. No. 62/692,568 filed Jun. 29, 2018, the disclosures of which are incorporated herein by reference in their entireties, including Exhibits A-C attached thereto.

FIELD OF THE INVENTION

The present disclosure relates generally to systems, methods, and devices for gait analysis and training, and, more particularly, to a wearable, autonomous apparatus for quantitative analysis of a subject's gait and/or providing feedback for gait training of the subject. Particular applications of interest arise in sport performance assessment and elderly care.

BACKGROUND OF THE INVENTION

Pathological gait (e.g., Parkinsonian gait) is clinically characterized using physician observation and camera-based motion-capture systems. Camera-based gait analysis may provide a quantitative picture of gait disorders. However, camera-based motion capture systems are expensive and are not available at many clinics. Auditory and tactile cueing (e.g., metronome beats and tapping of different parts of the body) are often used by physiotherapists to regulate patients' gait and posture. However, this approach requires the practitioner to closely follow the patient and does not allow patients to exercise on their own, outside the laboratory setting.

Compared to traditional laboratory equipment for gait analysis, instrumented footwear systems are more affordable and versatile. These devices can be used to assess the wearers' gait in unrestricted environments, in diverse motor tasks, and over extended time periods.

Quantitative gait analysis is a powerful diagnostic tool for physicians treating patients with gait disorders. Athletic trainers often rely on assessments of the running gait when coaching professional athletes who are recovering from an injury or want to improve their performance. Quantitative gait analysis requires specialized laboratory equipment such as optical motion capture systems and treadmills instrumented with force plates or other force mapping systems. For this reason, the use of gait analysis is currently limited by high operating costs and lack of portability.

In recent years, several instrumented footwear systems have been developed for portable gait assessments. Compared to traditional laboratory equipment, these new systems are more affordable and versatile. However, the amount of parameters these devices can assess is still limited, and their accuracy is usually poor and not comparable to that of standard laboratory equipment.

OBJECTS OF THE INVENTION

Certain prior art devices are incapable of estimating the user's center of mass (COM) and dynamic margin of stability (MOS). It is therefore an object of the present invention to quantify the position of the COM, the MOS and other indices of dynamic stability. This object is met by the present invention's use of insoles instrumented with inertial, piezoresistive and time-of-flight proximity sensors.

It is another object of the present invention to measure the coordination between upper and lower extremities, as well as to measure a broad set of kinematic and kinetic gait parameters, including, for example, inter-limb parameters such as double support time.

Yet another object of the present invention is to provide wireless functionality and to be lightweight (i.e., below 100 grams) and affordable (i.e., $500 or less), while simultaneously featuring a high sampling rate (500 Hz), making it superior for highly dynamic tasks.

Another object of the present invention is to provide a broad set of information, including plantar pressure maps and center-of-pressure (CoP) trajectories, that can be used for both performance tracking and injury prevention.

Yet another object of the present invention is to make it possible to create remotely-monitored, self-administered walking and balance exercises for the elderly which can potentially increase safety and relieve the financial burden on the healthcare system.

Another object is to provide a completely wireless and portable interface that allows the wearer's own shoes to be retrofitted with the present invention, thereby eliminating the need to modify the shoes themselves.

Yet another object of the invention is to circumvent conventional limitations of portable gait-monitoring systems by presenting novel calibration algorithms based on machine learning and biomechanical models of human locomotion.

A further object of the invention is to enable sport performance evaluation (e.g., running technique) and clinical gait assessments in patients with movement disorders.

Additional objects of the invention include: providing fall risk assessment and fall detection in the elderly, aiding injury prevention in athletes and in the elderly, offering gait or balance rehabilitation with real-time augmented feedback, generating monitoring or activity classification for vulnerable older adults, and aiding pedestrian navigation.

SUMMARY

The present invention is an improvement over and/or a supplement to the systems, devices and methods disclosed U.S. Patent Application Publication No. 2017/0055880, the contents of which are incorporated by reference herein. More particularly, the device of the present invention measures a broad set of spatio-temporal gait parameters (e.g., stride length, foot-ground clearance, foot trajectory, cadence, single and double support times, symmetry ratios and walking speed), as well as kinetic parameters (i.e., dynamic plantar pressure maps, CoP trajectories) during different tasks (e.g., walking and running tasks). By applying custom calibration algorithms (see, for example, FIGS. 1 and 2, which are referenced and described in greater detail hereinbelow) to the raw data measured by the embedded sensors, the device can assess all gait parameters within 1-2% accuracy. This feature allows the present invention to capture subtle changes in gait parameters that are known precursors of injuries or imbalance, and to precisely assess an athlete's running technique.

A system assembled in accordance with the present invention utilizes affordable, mid-level sensors, while providing the option of auditory and vibro-tactile feedback that can be utilized by a user for gait rehabilitation. Another application for the data collected by the system is activity monitoring/classification. This can be realized with machine learning models to automatically classify activities of daily living based on the signals recorded by the system. Additionally, the system can potentially be used with a smartphone equipped with GPS to realize a portable navigation system. Higher accuracy for the system is achieved through the calibration algorithms referenced above and described in greater detail in attached FIGS. 1 and 2. Higher accuracy makes it possible to detect subtle changes in the user's gait, which can be precursors of imbalance or injuries.

Most existing portable devices cannot simultaneously estimate temporal parameters, spatial parameters, and kinetic parameters. Although a few such devices may be able to achieve this goal, they suffer from a limited sample rate, which makes them unsuitable for assessments of highly dynamic tasks. Additionally, these devices cannot estimate some important gait parameters, such as foot-ground clearance, foot trajectory, single and double support times, symmetry ratios, CoP trajectories, etc., making them unsuitable for clinical gait assessments.

Traditional gait analysis systems for clinical assessments and sport performance assessments require expensive laboratory equipment, including force plates and optical motion capture systems. Portable gait analysis systems have the advantage of being lightweight and cost-effective, and are not constrained to the laboratory environment, thus making it possible to assess gait metrics in daily-life scenarios. This has important implications for clinical diagnostics, activity monitoring, as well as performance evaluation in sports.

BRIEF DESCRIPTION OF FIGURES

For a more complete understanding of the present disclosure, reference is made to the following drawings, in which.

DETAILED DESCRIPTION OF EXEMPLARY EMBODIMENTS

Figure 1:
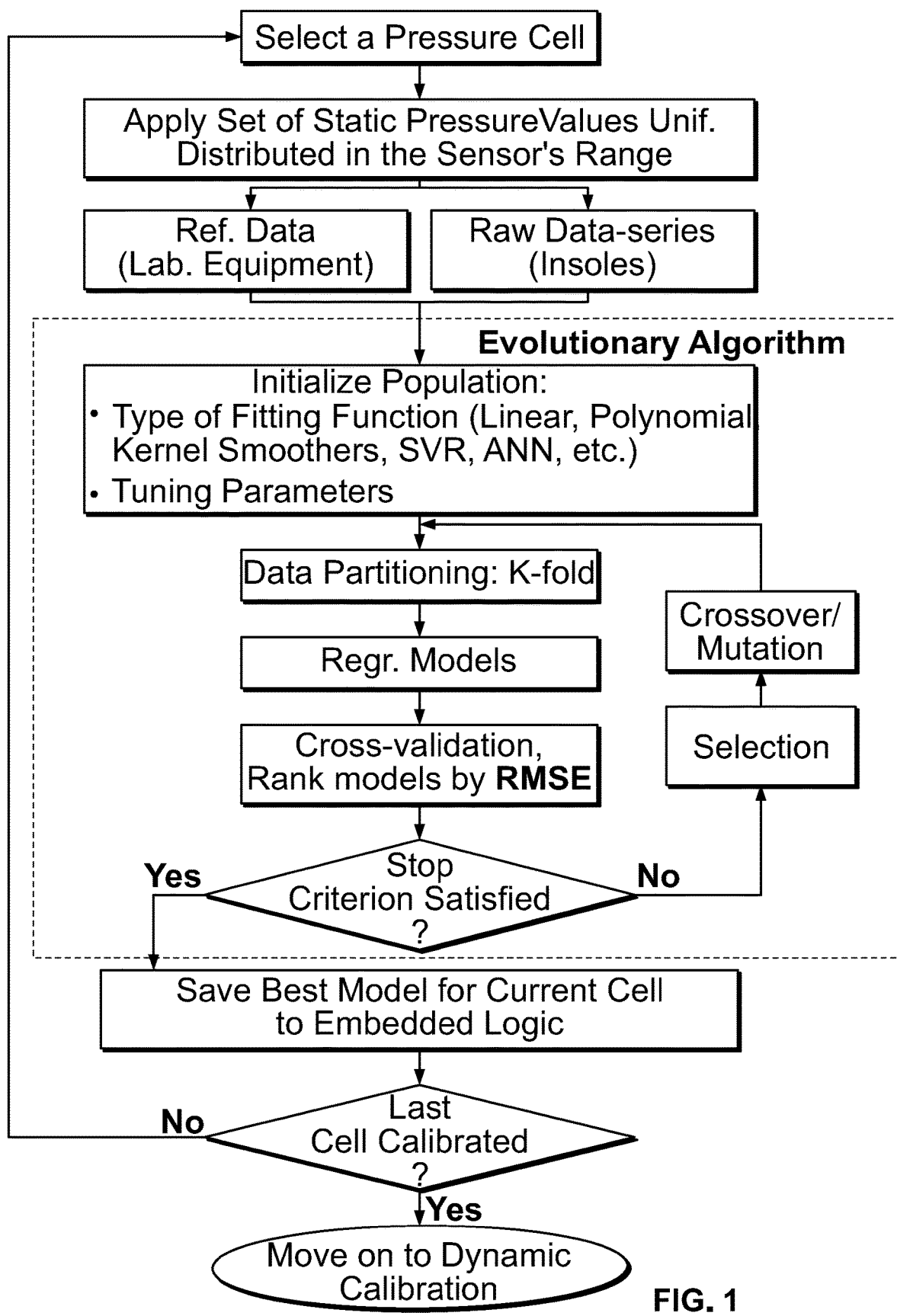
FIG. 1 is a schematic illustration of the first step of a novel two-step calibration approach for the CoP, illustrating a static calibration framework for multi-cell pressure insoles.
Figure 2:
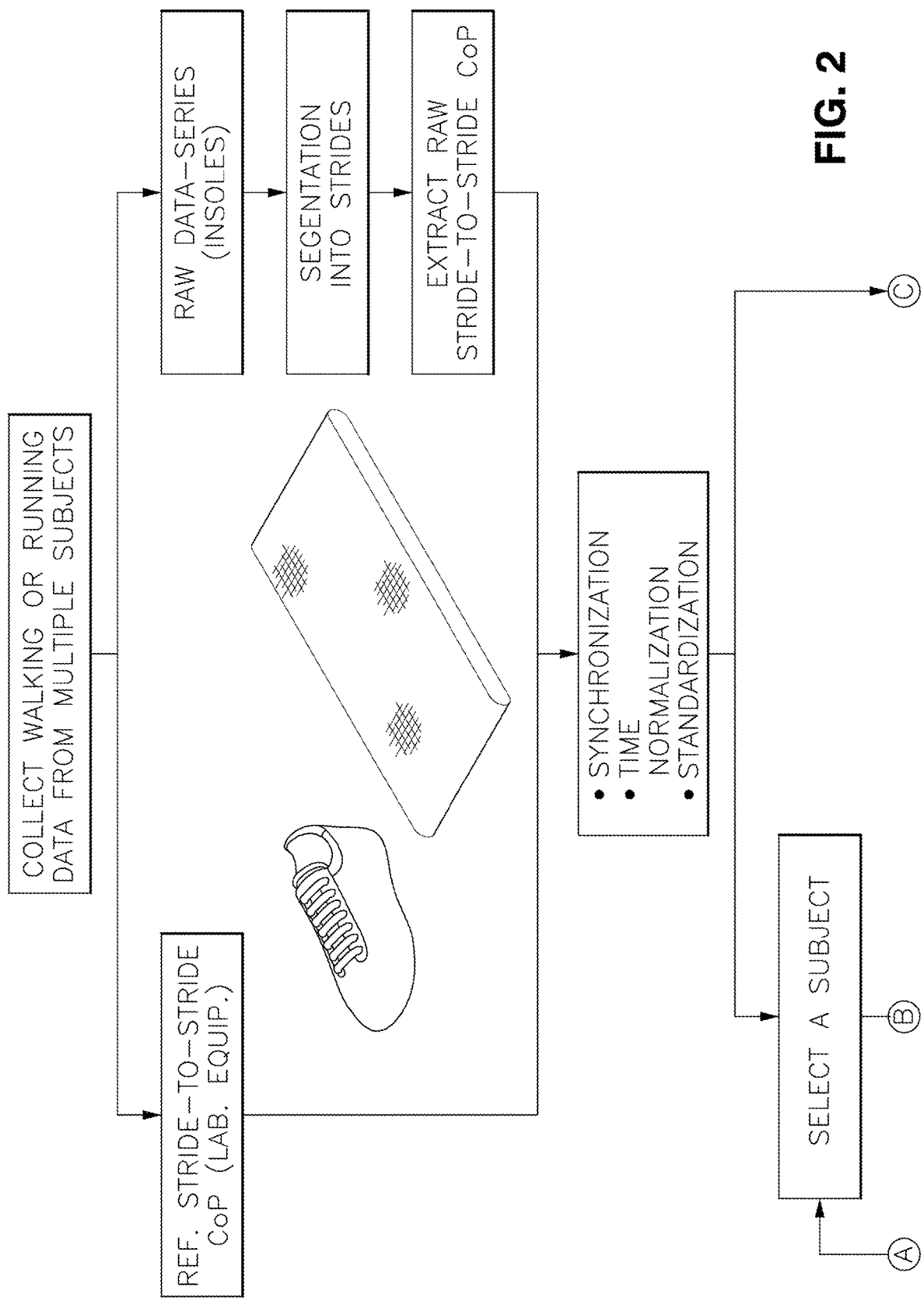
FIG. 2 is a schematic illustration of the second step of a novel two-step calibration approach for the CoP, illustrating a dynamic calibration framework for CoP trajectories.
Figure 2:
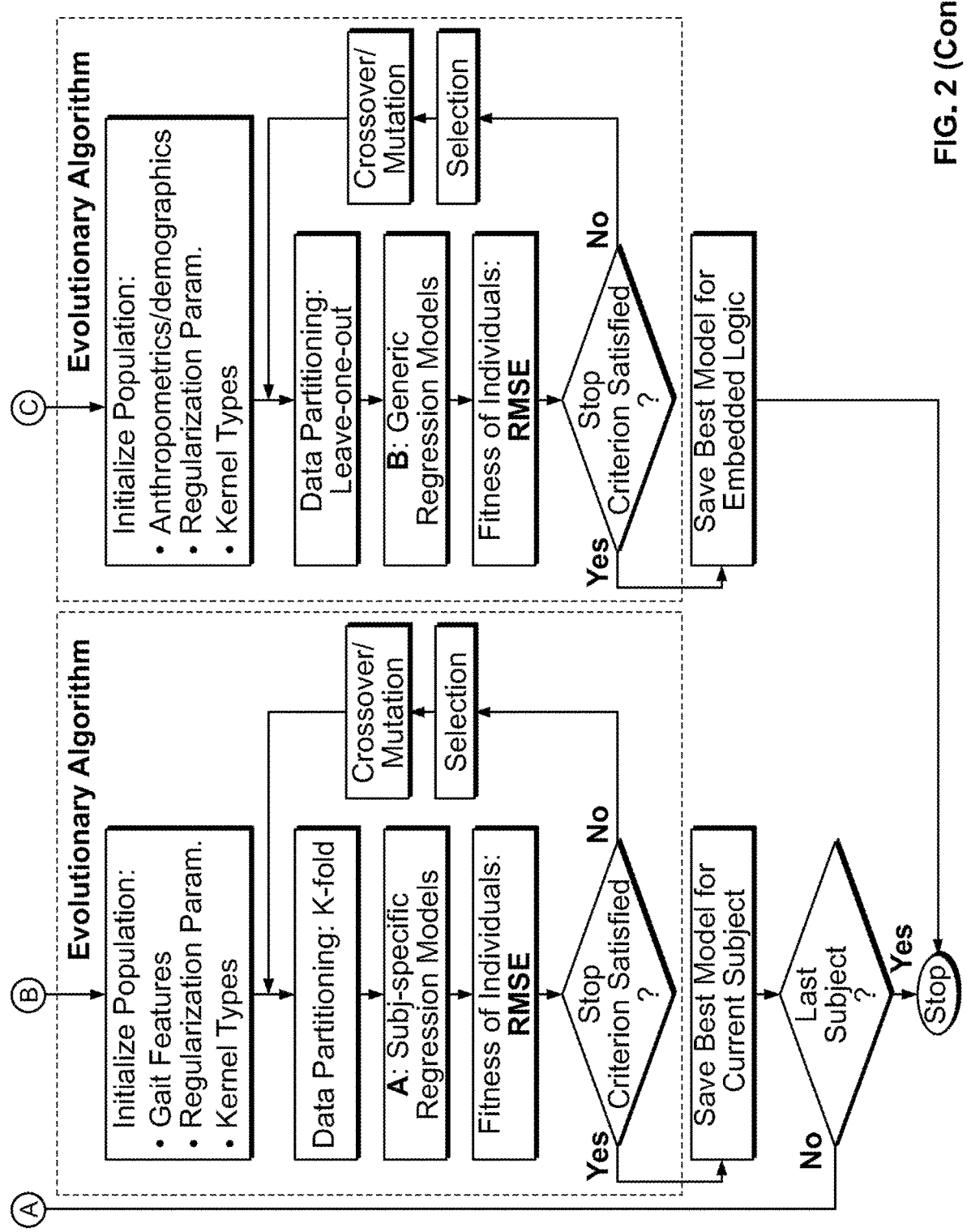

In an embodiment, the present invention is a device comprising two insole modules and a data logger. Each insole module is wireless, having a transmission unit, as well as the ability to accurately measure kinematic and kinetic gait parameters of a user in a variety of dynamic tasks (e.g., walking, running, negotiating stairs, etc.), both outdoor and indoor. In an embodiment, all the data are collected at 500 Hz and sent wirelessly to a battery-powered single-board computer (or mobile device) running a data-logger. In an embodiment, the single-board computer fits inside a running belt that can be worn by the user or can be optionally located offboard within a 30-meter range from the user.

In an embodiment, each insole module consists of an eight-cell piezoresistive sensor, a nine degree-of-freedom inertial sensor, and a custom-made logic unit. The pressure sensors are located, for instance, underneath the calcaneous, the lateral arch, the head of the first, third and fifth metatarsals, the hallux, and the toes, while the inertial sensor is placed, for instance, along the midline of the foot.

In an embodiment, the logic unit includes a microcontroller interfaced with the multi-cell pressure sensor through an eight-channel multiplexer, while communicating with the inertial sensor through a serial connection. In an embodiment, all the data are sampled at 500 Hz and sent through UDP over WLAN to the single-board computer by means of a Wi-Fi module. The logic unit, which can be housed in a plastic enclosure, is powered by, for instance, a small 400 mAh Li-po battery through a step-up voltage regulator.

In an embodiment, the single-board computer runs a Linux distribution with a real-time kernel operating in headless mode. A miniature Wi-Fi router can be connected to the computer, serving as an access point. In use, for example, the computer synchronizes the data incoming from the insole modules and writes them to a micro-SD card. The same data can also be streamed at a lower sample rate (50 Hz) to an easy-to-use user interface running on the user's laptop or mobile phone, whereby the interface allows the user to control the device remotely and to visualize measured data.

Other features, attributes and exemplary embodiments of the present invention are disclosed and illustrated in the publication by Huanghe Zhang et al., titled "Estimating CoP Trajectories and Kinematic Gait Parameters in Walking and Running Using Instrumented Insoles," IEEE Robotics and Automation Letters, Vol. 2, No. 4, October 2017, pp. 2159-2165, and in the publication by Huanghe Zhang et al., titled "Regression Models for Estimating Kinematic Gait Parameters with Instrumented Footwear," IEEE International Conference on Biomedical Robotics and Biomechatronics, August 2018, both publications being incorporated by reference herein in their entireties and therefore constituting part of the present application. In addition to the incorporation by reference immediately above, it is noted that the former publication identified above was attached as Exhibit B in the related provisional U.S. patent application referenced above and incorporated by reference herein. With regard to the latter publication identified above, an earlier, unpublished version was attached as Exhibit C to the aforementioned provisional U.S. patent application.

It will be understood that the embodiments described in the foregoing specification and claims, as well those described in the various documents incorporated by reference herein, are merely exemplary and that a person skilled in the art may make many variations and modifications without departing from the spirit and scope of the present invention.

We claim:

1. A method for calibrating a gait measurement system, comprising the steps of:
   i) providing an instrumented insole having a plurality of pressure-sensing cells;
   ii) exerting a fixed, uniform pressure on said instrumented insole;
   iii) recording a respective output for each of said pressure-sensing cells in response to pressure exerted on said instrumented insole during the performance of step (ii);
   iv) applying a plurality of fitting functions to said respective output of each of said pressure-sensing cells, thereby obtaining a plurality of respective model data; and
   v) applying cross validation to said plurality of respective model data to obtain a calibration model for each of said pressure-sensing cells.

2. The method of claim 1, wherein at least one pressure-sensing cell of said plurality of pressure-sensing cells comprises a piezoresistive sensor.

3. The method of claim 1, wherein said plurality of pressure-sensing cells includes eight pressure-sensing cells.

4. The method of claim 1, further comprising the step of locating at least some of said plurality of pressure-sensing cells beneath a user's calcaneous, a user's lateral arch, a head of a user's first metatarsal, a head of a user's third metatarsal, a head of a user's fifth metatarsal, a user's hallux and/or a user's toes.

5. The method of claim 1, further comprising the step of retrofitting said instrumented insole to a shoe of a user.

6. The method of claim 1, further comprising the step of providing said instrumented insole with an inertial sensor.

7. The method of claim 6, wherein said inertial sensor has nine-degrees of freedom.

8. The method of claim 6, further comprising the step of locating said inertial sensor along a portion of said instrumented insole corresponding to a midline of a user's foot.

9. The method of claim 1, further comprising the step of providing vibro-tactile feedback to a user from said instrumented insole.

10. The method of claim 1, further comprising the step of providing said instrumented insole with a logic unit configured to sample data at 500 Hertz.

11. The method of claim 1, further comprising the step of estimating center of pressure and/or dynamic margin of stability.

12. The method of claim 1, further comprising the step of measuring inter-limb parameters.

13. The method of claim 1, further comprising the step of measuring one or more gait parameters selected from the group consisting of stride length, foot-ground clearance, foot trajectory, cadence, double support time, single support time, walking speed, center of pressure, and margin of stability.

14. The method of claim 13, further comprising the step of generating dynamic plantar pressure maps and/or center of pressure trajectories.

15. The method of claim 1, further comprising the step of classifying activities of daily living.

16. The method of claim 1, wherein said method is implemented in connection with a mobile device having GPS in order to realize a portable navigation system.

17. The method of claim 1, further comprising the steps of remotely monitoring and administering walking and/or balance exercises.

18. The method of claim 1, wherein said method is implemented in a device used for gait and/or balance rehabilitation.

19. A method for calibrating a gait measurement system, comprising the steps of:
   i) providing an instrumented insole and a reference source;
   ii) recording a first data set from said instrumented insole and a second data set from said reference source;
   iii) computing center of pressure trajectories from said first data set and said second data set;
   iv) validating said center of pressure trajectories using one or more regression models; and
   v) calibrating said instrumented insole via said first data set and said second data set.

20. The method of claim 19, further comprising the step of retrofitting said instrumented insole to a shoe of a user.

21. The method of claim 19, further comprising the step of providing said instrumented insole with an inertial sensor.

22. The method of claim 21, wherein said inertial sensor has nine-degrees of freedom.

23. The method of claim 21, further comprising the step of locating said inertial sensor along a portion of said instrumented insole corresponding to a midline of a user's foot.

24. The method of claim 19, further comprising the step of providing vibro-tactile feedback to a user from said instrumented insole.

25. The method of claim 19, further comprising the step of providing said instrumented insole with a logic unit configured to sample data at 500 Hertz.

26. The method of claim 19, further comprising the step of estimating center of pressure and/or dynamic margin of stability.

27. The method of claim 19, further comprising the step of measuring inter-limb parameters.

28. The method of claim 19, further comprising the step of measuring one or more gait parameters selected from the group consisting of stride length, foot-ground clearance, foot trajectory, cadence, double support time, single support time, walking speed, center of pressure, and margin of stability.

29. The method of claim 28, further comprising the step of generating dynamic plantar pressure maps and/or center of pressure trajectories.

30. The method of claim 19, further comprising the step of classifying activities of daily living.

31. The method of claim 19, wherein said method is implemented in connection with a mobile device having GPS in order to realize a portable navigation system.

32. The method of claim 19, further comprising the steps of remotely monitoring and administering walking and/or balance exercises.

33. The method of claim 19, wherein said method is implemented in a device used for gait and/or balance rehabilitation.

* * * * *